United States Patent [19]

Brown

[11] 4,082,810
[45] Apr. 4, 1978

[54] BULKY TRIALKYLBOROHYDRIDES

[75] Inventor: Herbert C. Brown, West Lafayette, Ind.

[73] Assignee: Aldrich-Boranes, Inc., Milwaukee, Wis.

[21] Appl. No.: 622,985

[22] Filed: Oct. 16, 1975

Related U.S. Application Data

[63] Continuation-in-part of Ser. No. 114,084, Feb. 9, 1971, abandoned.

[51] Int. Cl.$^2$ ............................................. C07F 5/02
[52] U.S. Cl. ............................................. 260/606.5 B
[58] Field of Search ................................ 260/606.5 B

[56] References Cited

U.S. PATENT DOCUMENTS 3,163,679  12/1964  Koster .................. 260/606.5 B
3,867,460  2/1975  Corey .................. 260/606.5 B

OTHER PUBLICATIONS

Brown, et al., JACS 91, 4304-4305, (1969).
Brown, et al., JACS 92, 709-710, (1970).
Binger, et al., Ann 717, 27 to 30, 37-39, (1968).
Brown, et al., JACS 75, 194-195, (1953).

*Primary Examiner*—Helen M. S. Sneed
*Attorney, Agent, or Firm*—Albert Tockman; John J. Kolano

[57] ABSTRACT

Borohydride hydrogenations using agents of the formula M[RR'R"BH] wherein M is a metal and R, R', and R" are each organic groups, at least one of them being a secondary or tertiary alkyl group, are described herein. These compounds are active hydrogenating agents which are particularly useful because they permit steric control of the hydrogenation of carbonyl groups, they permit selective hydrogenation of functional groups or, where one of the R groups is optically active, they permit stereoselective hydrogenation.

9 Claims, No Drawings

BULKY TRIALKYLBOROHYDRIDES

Application Ser. No. 479,776 is a continuation-in-part of application Ser. No. 114,084, filed Feb. 9, 1971 now abandoned.

A variety of reducing agents have been described in the literature but these do not provide steric control of reaction. That is, they are not selectively active. That means that, where the reduction introduces a new asymmetric center, a mixture of isomers is obtained, although one of the isomers may be favored somewhat. In addition, where several reducible groups are present in the molecule, they are not selectively reducible. These agents include simple borohydrides like sodium borohydride; acid agents such as diborane; alkyl borohydrides such as Li(CH$_3$)$_3$BH; and alkoxy borohydrides such as lithium and sodium trimethoxyborohydride. The same is true for aluminohydrides such as lithium tri-t-butoxyaluminum hydride. Dialkylboranes, where the two alkyl groups are bulky, do provide some steric control but the reaction can be particularly slow when the alkyl groups are bulky.

The present invention relates to the fact that metal borohydrides, wherein the boron atom is substituted by one or more bulky alkyl groups are not only hydrogenating agents, but they are also much more rapid hydrogenating agents than the corresponding substituted alkyl boranes and they also unexpectedly provide selective hydrogenation too. That is, hydrogenations are relatively slow with dialkylboranes but comparatively fast with these substituted borohydrides. Actually, the specific rate of any reaction can vary, depending on the particular compound being hydrogenated. Thus, hydrogenation with the bulky alkylboranes is often still incomplete after 24 hours whereas hydrogenation with the corresponding borohydride under similar conditions gives almost complete hydrogenation in less than 15 minutes. When the structure of the compound being hydrogenated is such that hydrogenation with the alkylborane takes place readily at room temperature, the corresponding borohydrides are still advantageous in that they would permit the hydrogenation to be carried out at low temperatures (−70° C.) which would permit more selective hydrogenation.

As far as the selectivity of the reaction is concerned, where the reaction produces an asymmetric center, one isomer is obtained almost exclusively. In the situation where several hydrogenatable functional groups are present in the molecule or in a mixture, the least hindered group is hydrogenated preferentially before there is significant attack on other hydrogenatable functional groups. Thus, control of the amount of borohydride added to the reaction mixture will provide control of the extent of hydrogenation that takes place. Use of an excess of the borohydride would give full hydrogenation of all hydrogenable groups present. The course of the reaction here can be followed using IR or NMR spectroscopy and chromatography. Finally, if the bulky alkyl groups contain an asymmetric center, use of one stereoisomer can serve to provide the desired configuration in the final products. Thus, if such a borohydride is used to hydrogenate a ketone which is itself optically inactive but which gives, on hydrogenation, an alcohol which can be optically active, the actual alcohol obtained will depend on the stereoisomer of the borohydride used. If the ketone is itself a dl-compound, only one of the ketone isomers will be reduced preferentially with the predominant formation of a single alcohol isomer.

The borohydrides found useful in such hydrogenations have the following general formula

In the above borohydrides, M[RR'R"BH], M is a strongly cationic metal. That is M is a metal which forms a readily stable cation, it is not readily reduced from the desired cation stage to the free metal, and it forms a relatively stable organo-metallic compound, M-Org, which exhibits the ability to add to the carbonyl groups of aldehydes and ketones. It also forms stable borohydrides, MBH$_4$. More particularly, M is selected from the group consisting of alkali metals, alkaline earth metals, Mg-halogen wherein the halogen has an atomic weight greater than 30, and tetramethylammonium. Typical representatives of the "strongly cationic metals" are the alkali metals, i.e., lithium, sodium, potassium, rubidium and cesium; the alkaline earth metals, such as magnesium, calcium, strontium, and barium. Where the metal M forms an ion with a valence of 2, the metal is then associated with the corresponding number of [RR'R"BH] units in the borohydride or it can be associated with one [RR'R"BH] group with some simple anion such as halide satisfying the remaining valence in such a mixed ion. Thus, for example, M can be MgCl or MgBr.

The groups R, R' and R" are selected in such a manner that at least one of them is a bulky alkyl group wherein the attachment to the boron is through a secondary or tertiary carbon atom. Thus, such a bulky group must contain at least 3 carbon atoms. Groups suitable for this purpose include isopropyl, sec-butyl, 2-pentyl, siamyl, and thexyl. Cycloalkyl can also be used for this purpose. This includes simple cyclic groups such as cyclopentyl and cyclohexyl; bicyclic groups such as isopinocampheyl and norbornyl; and polycyclic groups such as tetralyl and steroids such as cholestan-6-yl. The term cycloalkyl, as used in this invention, is intended to encompass all three types of ring systems.

The various R groups can be further combined to give cyclic structures. Thus, if two of the R groups are combined into simple groups such as tetramethylene and pentamethylene, simple ring systems containing a boron atom such as boracyclopentane and boracyclohexane are obtained. If two of the R groups are combined in a cyclic structure, such as p-menth-2,9-ylene and cyclooct-1,5-ylene, bicyclic boranes and borohydrides result. Finally, if all three R groups are combined, such as in cyclododeca-1,5,9-triyl, a polycyclic borane or borohydride results. It should be noted that the rings formed, including the boron, preferably contain 5 or 6 carbon atoms.

Where a bulky group is not necessary, the R groups can be groups such as methyl and ethyl.

In addition to the alkyl and cycloalkyl groups referred to earlier, R" can be an aryl group such as phenyl and naphthyl; an alkoxy group such as methoxy, ethoxy and t-butoxy; cycloalkoxy such as cyclohexyloxy; aryloxy such as phenoxy and naphthyloxy; alkyl- and arylthio such as thio-t-butoxy and phenylthio; dialkyl- and diarylamino groups such as dimethylamino, piperidino, and diphenylamino; and dialkyl- and diarylphosphino groups such as dimethylphosphino and diphenylphosphino.

The various alkyl, cycloalkyl, and aryl groups referred to above with regard to R, R' and R'' can be further substituted with unreactive substituents. That is, R, R' and R'' can be further substituted with groups that are compatible with the borohydride materials. Because of the reactive nature of borohydrides, the list of possible substituents is rather limited and includes alkyl groups such as methyl and ethyl; aryl groups such as phenyl and naphthyl; alkoxy groups such as methoxy and ethoxy; cycloalkoxy groups such as cyclohexyloxy; aryloxy groups such as phenoxy; arylthio groups such as phenylthio; cycloalkylthio groups such as cyclohexylthio; dialkylamino groups such as dimethylamino; diarylamino groups such as diphenylamino; dialkylphosphino groups such as dimethylphosphino; and diarylphosphino groups such as diphenylphosphino. Examples of groups containing such additional substituents are 2-methoxyethoxy, 2-methylcyclopentyl, α-phenylethyl, tolyl, anisyl, 4-t-butylphenoxy and thioanisyl. When reference is made to substituted groups for R, R' and R'', it should be understood to mean unreactive substituents of the type described above.

Several general methods are available for the preparation of the borohydrides referred to in the present invention. Thus, a disubstituted borane can be reacted with an organometallic compound as follows:

$$RR'BH + MR'' \rightarrow M[RR'R''BH]$$

MR' in the above case can be a Grignard reagent in which case M represents MgCl or a similar group. The above procedure can also be used when R'' is alkoxide or a similar group. In many cases, this procedure results in rearrangements and gives mixtures of products.

In an alternate preferred procedure, a trisubstituted borane is reacted with an alkali metal hydride as follows:

$$RR'R''B + MH \rightarrow M[RR'R''BH]$$

Finally, in another method, a trisubstituted borane can be reacted with an alkali metal hydride derivative such as lithium trimethoxyaluminohydride as follows:

$$RR'R''B + LiAlH(OCH_3)_3 \rightarrow Li[RR'R''BH] + Al(OCH_3)_3$$

These two methods are preferred because they give pure M[RR'R''BH] end products.

When the above procedures are used to prepare lithium compounds, the following comments are applicable. The addition of lithium hydride to hindered trialkylboranes, RR'R''B, to form the desired lithium trialkylborohydrides, Li[RR'R''BH] is often very slow. For example, a mixture of tri-sec-butylborane and lithium hydride is heated under reflux in tetrahydrofuran for several hours without significant reaction although reaction occurs with longer reaction time. An alternative synthesis is to add the alkyllithium to the desired dialkylborane at low temperatures. Then the desired trialkylborohydride is formed rapidly and any rearrangement is minimized. Alternatively, tri-sec-butylborane can be treated with lithium trimethoxyaluminohydride. The desired borohydride is then formed rapidly in high purity. These three specific reactions can be depicted as follows:

$$(sec\text{-}Butyl)_3B + LiH \xrightarrow{slow} Li(sec\text{-}Butyl)_3BH$$

$$(sec\text{-}Butyl)_2BH + sec\text{-}butylLi \xrightarrow{fast} Li(sec\text{-}Butyl)_3BH$$

$$(sec\text{-}Butyl)_3B + LiAlH(OCH_3)_3 \xrightarrow{fast} Li(sec\text{-}Butyl)_3BH + Al(OCH_3)_3$$

In this way it becomes possible to synthesize readily a wide range of trialkylborohydrides containing bulky organic groups, as illustrated for the synthesis of lithium diisopinocampheylmethylborohydride and similar derivatives.

It should be noted that, although the present products are specifically depicted as borohydrides, it is not necessary to isolate these materials in order to use them. That is, they can be prepared and isolated as such or they can be prepared in situ without specifically isolating them from the reaction mixture. In the latter situation, only a small amount of the borohydride may be present in the reaction mixture at one particular time as the result of the addition of the strong base to the borane. However, under possible equilibrium conditions, as borohydride is used up in hydrogenation, additional borohydride is formed in the reaction mixture. For the purposes of this invention, such a gradual formation of the borohydride is considered to be equivalent to the borohydride as formed by direct reaction with actual isolation.

The substituted boranes used as the starting materials in the above procedure are conveniently prepared by the reaction of an appropriate olefin with borane or an appropriately substituted borane. Details of the procedures involved have been described in the literature.

The borohydrides referred to herein act on a variety of hydrogenatable functional groups. The hydrogenatable functional groups involved can contain single, double or triple bonds. More particularly, the hydrogenatable functional groups are selected from the group consisting of alkyl halides, alkyl esters of sulfonic acids; functional groups containing a double or triple bond including carbon or nitrogen and also including an atom other than hydrogen and carbon; epoxides and disulfides.

More particularly, a wide variety of specific functional groups can be readily hydrogenated by the borohydrides of the present invention. Thus, cycloalkyl halides are hydrogenated to cycloalkanes; alkyl arenesulfonates are hydrogenated to alkanes; aldehydes, ketones, and acid chlorides are hydrogenated to alcohols; quinones are hydrogenated to hydroquinones; epoxides are hydrogenated to alcohols; lactones are hydrogenated to diols; carboxylic acid salts and carboxylic acid esters are hydrogenated to alcohols; thioesters are hydrogenated to alcohols; carboxylic acid amides and nitriles are hydrogenated to amines; oximes are hydrogenated to hydroxylamines; imines are hydrogenated to amines; nitro, nitroso, and azo compounds are hydrogenated to amines; and disulfides are hydrogenated to mercaptans.

More specifically, the compounds described in the present application are rapid and powerful hydrogenating agents. Thus, the present borohydrides react rapidly and smoothly with halides to give the corresponding hydrocarbons. For example, methyl iodide is hydrogenated to methane, benzyl bromide is hydrogenated to toluene, and chloromethylmethyl ether is hydrogenated to dimethyl ether. Alkylene oxides such as cyclohexene oxide are hydrogenated readily to cyclohexanol. Ketones such as camphor are rapidly hydrogenated. The hydrogenations take place smoothly and rapidly which is surprising in view of the slow reactivity of the related boranes. Those trialkylborohydrides containing one or more bulky alkyl groups are also surprisingly more reactive than borohydrides without such bulky groups.

A particularly preferred embodiment of the present invention is the use of the borohydrides described herein for the hydrogenation of ketones. Thus, the present compounds further react with ketones to give a predominance of one isomer. For example, lithium perhydro-9b-boraphenalylhydride reacts with camphor to give a quantitative yield of 99% isoborneol. The same hydride reacts with 2-methyleyclopentanone to give cis-2-methylcyclopentanol of 94% epimeric purity. In contrast, sodium borohydride reduction of 2-methylcyclopentanone gives only 31% of the cis-epimer while lithium tri-n-butylborohydride, which has the same number of carbon atoms as the phenalyl compound but as three long alkyl groups attached to the boron, gives only 67% of the cis-epimer.

As far as selectivity when several hydrogenatable groups are present is concerned, lithium perhydro-9b-boraphenalylhydride reacts with the ditosylate of 2,4,4-trimethyl-1,5-pentanediol to reduce the less hindered function and give 2,2,4-trimethyl-1-pentanol tosylate. Similarly, 3,3-dimethyl-2,5-hexanedione is reduced to 3,3-dimethyl-5-hydroxy-2-hexanone.

It should be noted that, although illustrations are provided showing the activity of the present compounds in hydrogenations involving relatively simple compounds, these are intended to be illustrative of similar reactions with more complex molecules.

Reactions using the present borohydride reagents can be carried out in a variety of inert solvents, i.e., solvents which are inert to the reducing action of the reagents. Ethers and aliphatic or aromatic hydrocarbons are useful for this purpose. Tetrahydrofuran and ethylene glycol dimethyl ether are somewhat preferred solvents because they promote a faster time of reaction but other solvents such as ethyl ether, hexane, and benzene are also satisfactory. The temperature at which the reaction is carried out is not critical. For convenience, it may be preferable to carry out the reduction between 0° C. and room temperature but temperatures as low as a Dry Ice bath or as high as the reflux temperature of the solvent can also be used.

The following examples are presented to specifically illustrate the present invention but should not be construed as limiting it in any way. Thus, other borohydrides can be prepared by the procedures described and other reductions can be carried out in the manner described. In the examples, quantities are given in millimoles (mmoles), volumes in milliliters (ml.), and temperatures in degrees Centigrade (0° C.).

EXAMPLE 1

In a flask is placed 100 mmoles of 9-borabicyclo[3.3.1]nonane in 200 ml. of tetrahydrofuran, cooled to −78° C, and treated with 100 mmoles of methyllithium in ethyl ether. A solution of lithium B-methyl-9-borabicyclo[3.3.1]nonanehydride results.

If 100 mmoles of methyl iodide is added to the above solution, a rapid evolution of methane takes place and the reaction is essentially complete in 10 minutes.

If 9-borabicyclo[3.3.1]nonane is reacted with n-butyllithium, isopropyllithium, t-butyllithium, phenyllithium and p-tolyllithium according to the above procedure, the corresponding B-substituted compound is obtained in each instance. Each of these borohydrides reacts rapidly with methyl iodide to give methane.

Similarly, 9-borabicyclo[3.3.1]nonane reacts with dimethylmagnesium, methylmagnesium chloride, cyclohexylmagnesium chloride, and phenylmagnesium chloride to give the corresponding magnesium borohydride in each instance. Likewise, 9-borabicyclo[3.3.1]-nonane can react with ethyl sodium or ethyl potassium to give the corresponding sodium and potassium borohydride.

In addition, potassium t-butoxide, tetramethylammonium phenoxide, sodium cyclohexyloxide, sodium 2-methoxyethoxide, sodium 2-(2-methoxyethoxy)ethoxide, sodium thiomethoxide, lithium diethylamide, and lithium di-n-butylphosphide each react with 9-borabicyclo[3.3.1]nonane by the above procedure to give the corresponding borohydride. Specifically, potassium t-butoxide gives potassium B-t-butoxy-9-borabicyclo-[3.3.1]nonanehydride. Each of these hydrides readily reduces methyl iodide to methane.

EXAMPLE 2

In a flask is placed 100 mmoles of boracyclohexane in 200 ml. of tetrahydrofuran and treated with isopropyllithium in ethyl ether. A solution of lithium B-isopropylboracyclohexane results.

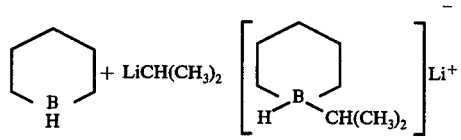

Addition of 100 mmoles of methyl iodide to the above solution results in a rapid evolution of methane and the reaction is essentially complete in 10 minutes.

Similarly, sec-butyllithium, t-butyllithium, cyclohexyllithium, and cyclohexylmagnesium chloride are used to give the corresponding cyclic borohydride containing a bulky alkyl or cycloalkyl group attached to boron through a secondary or tertiary carbon atom.

EXAMPLE 3

In a flask is placed 100 mmoles of borane in 50 ml. of tetrahydrofuran. The flask is cooled to 0° C. and 200 mmoles of optically active α-pinene is added. The resulting mixture is stirred under nitrogen for 1 hour to complete the hydroboration and give a solution of diisopinocampheylborane. Then, 100 mmoles of methyllithium in ethyl ether is added to give lithium methyldiisopinocampheylborohydride. Addition of methyl iodide results in rapid evolution of methane.

Cyclohexane and 2-methyl-2-butene are each reacted first with borane to give dicyclohexylborane and disiamylborane respectively. Each of these boranes are then reacted with methyllithium to give, respectively, lithium methyldicyclohexylborohydride and lithium methyldisiamylborohydride. Both of these borohydrides readily reduce methyl iodide to give methane.

If disiamylborane is reacted with n-butyllithium, isopropyllithium, t-butyllithium, phenyllithium and p-tolyllithium according to the above procedure, the correspondingly substituted lithium disiamylborohydride is obtained in each instance.

Similarly, disiamylborane reacts with dimethylmagnesium, methylmagnesium chloride, cyclohexylmagnesium chloride, and phenylmagnesium chooride to give the corresponding magnesium borohydride in each instance. Likewise disiamylborane is reacted with ethyl sodium and with ethyl potassium to give the corresponding potassium borohydride.

In addition, potassium t-butoxide, tetramethylammonium phenoxide, sodium cyclohexyloxide, sodium 2-methoxyethoxide, sodium 2-(2-methoxyethoxy)ethoxide, sodium thiomethoxide, lithium diethylamide and lithium di-n-butylphosphide each react with disiamylborane by the above procedure to give the corresponding borohydride.

EXAMPLE 4

Other borohydrides which can be prepared and used in a manner similar to that described in Example 3 are: lithium methyldi(sec-butyl)borohydride, lithium methylbis(2-methylcyclopentyl)borohydride, and lithium methylbis(2-methylcyclohexyl)borohydride. Use of methylmagnesium chloride in place of methyllithium gives the corresponding compounds in which lithium is replaced by MgCl.

In a similar manner, thexylborane is prepared and reacted with isobutylene or pipene to give, respectively, isobutylthexylborane and isopinocampheylthexylborane. If each of these boranes is reacted with methyllithium, the final products obtained are lithium methylisobutylthexylborohydride and lithium methylisopinocampheylthexylborohydride and lithium methylisopinocampheylthexylborohydride respectively. These compounds are also reducing agents.

EXAMPLE 5

In a flask is placed 100 mmoles of borane in 100 ml. of tetrahydrofuran. To the borane cooled to 0° C. is added 100 mmoles of D-(+)-limonene ($\alpha_D$+99°). Cyclic hydrocarbon takes place.

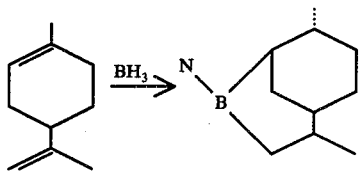

Addition of 100 mmoles of methyllithium forms the corresponding optically active trialkylborohydride. Alternatively, lithium ethyl, isopropyl, sec-butyl, t-butyl, and cyclohexyl can be added to give the corresponding borohydride.

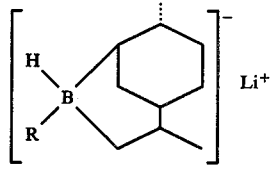

Addition of this reagent to secondary butyl bromide destroys one of the two optical isomers preferentially, giving a residual secondary butyl bromide that is optically active.

Addition of the reagent to acetophenone yields optically active α-phenylethyl alcohol.

EXAMPLE 6

In a flask is placed 100 mmoles of cis,cis,trans-perhydro-9b-boraphenalene and an excess (approximately 150 mmoles) of lithium hydride. The reaction mixture is heated under reflux for 1 hour and then filtered under nitrogen. Analysis of an aliquot establishes the presence of 100 mmoles of soluble "hydride" in the solution. Evaporation of the solvent leaves a residue which is an essentially quantitative yield of lithium perhydro-9b-boraphenalylhydride solvated by two molecules of tetrahydrofuran. Addition of methyl iodide to this material results in the immediate evolution of methane and regeneration of cis,cis,trans-perhydro-9b-boraphenalene. Similar results are obtained with cis,cis,trans-perhydro-9b-boraphenalene or with a mixture of isomers.

Similarly, sodium hydride and potassium hydride react to give the sodium and potassium perhydro-9b-boraphenalene hydrides and these can be used for sterically controlled reductions.

EXAMPLE 7

In a flask is placed 10 mmoles of 9-borabicyclo[3.3.1]nonane in tetrahydrofuran followed by 10 mmoles of methyllithium in ethyl ether to give a solution of lithium B-methyl-9-borabicyclo[3.3.1]nonanehydride. Then 10 mmoles of chlorodimethyl ether is added. Analysis of the mixture after 10 minutes shows a quantitative yield of dimethyl ether.

Reduction of benzyl bromide and allyl chloride by the above procedure gives excellent yields of toluene and propene respectively.

If phenyllithium, isopropyllithium, and t-butyllithium are substituted for methyllithium and the procedure of the first paragraph is repeated, the corresponding borohydride is formed in each instance. Reaction of each borohydride with chlorodimethyl ether gives dimethyl ether in essentially quantitative yield.

EXAMPLE 8

In a flask is placed 100 mmoles of 9-borabicyclo[3.3.1]nonane in tetrahydrofuran and 100 mmoles of methyllithium in ethyl ether is added. To the borohydride solution in the flask is addyd ethyl caproate and the mixture is allowed to stir for one hour at room temperature. A quantitative yield of 1-hexanol is obtained.

In similar manner, cyclohexene oxide is reduced rapidly to cyclohexanol.

The borohydride reducing agent described above also reduces aldehydes, ketones, quinones, acid chlorides, lactones, carboxylic acids, carboxylic acid salts, carboxamides, imides, oximes, nitriles, azo compounds, azoxy compounds, nitro compounds and nitroso compounds.

Similar results are obtained with lithium methyldicyclohexylborohydride, lithium methyldisiamylborohydride, Lithium methyldiisopinocampheylborohydride, lithium perhydro-9b-boraphenalylhydride, and the reaction product of lithium alkyls with the cyclic hydroboration product of limonene. Similar results are also obtained by using the corresponding sodium, potassium, magnesium, and calcium salts.

EXAMPLE 9

A solution of 10 mmoles of camphor in 2.5 ml. of tetrahydrofuran is added to 12.5 ml. of a 0.8M solution of lithium perhydro-9b-boraphenalylhydride in tetrahydrofuran at 0° C. After 30 minutes at 0° C., the reaction mixture is treated with 5 ml. of 3M aqueous sodium hydroxide, followed by 5 ml. of 30% hydrogen peroxide. The aqueous phase is saturated with potassium carbonate and the tetrahydrofuran layer is separated and analyzed by gas chromatography to show a quantitative yield of alcohol which is 99% isoborneol.

If lithium perhydro-9b-boraphenalylhydride is used to reduce 2-methylcyclopentanone by the method described above, the product obtained is cis-2-methylcyclopentanol with an epimeric purity of 94%. Similar results are obtained in the reduction of 2-methylcyclohexanone. Equally high stereoselectivities are realized with the sodium and potassium salts. Reduction of 2-methylcyclopentanone with the methyllithium or methylmagnesium chloride adducts of 9-borabicyclo[3.3.1]nonane, disiamylborane, dicyclohexylborane, diisopinocampheylborane and thexylisopinocampheylborane gives the cis-isomer in high purity. If optically active α-pinene is used to prepare the isopinocampheyl derivative used in the reduction, the product alcohol is optically active.

Equally satisfactory results are obtained in reducing simple aliphatic ketones, ketones derived from simple alicyclic systems, bicyclic ketones such as norcamphor and camphor and polycyclics such as steroids and alkaloids. In all cases these new reagents provide highly stereospecific steric control over the direction of reduction.

EXAMPLE 10

In a flask is placed 100 mmoles of 3,3-dimethyl-2,5-hexanedione in 50 ml. of tetrahydrofuran. The reaction mixture is cooled to 0° C. and 100 mmoles of lithium perhydro-9b-boraphenalylhydride is added slowly. A 90% yield of 3,3-dimethyl-5-hydroxy-2-hexanone is obtained.

Similarly, 100 mmoles each of 2-butyl bromide and 1-butyl bromide are placed in a flask in 100 ml. of tetrahydrofuran. To the flask, cooled to 0°, is added 100 mmoles of lithium perhydro-9b-boranberalylhydride. The reaction mixture is allowed to come to room temperature and stand overnight. Distillation yields an almost quantitative yield of 2-butyl bromide, with only traces of 1-butyl bromide.

The ditosylate of 2,4,4-trimethyl-1,5-pentanediol, 100 mmoles, is dissolved in 100 ml. of tetrahydrofuran and cooled to 0°. Then 100 mmoles of lithium perhydro-9b-borophenalylhydride is added and the mixture allowed to stand at room temperature for 24 hours. The reaction mixture is poured into water and extracted with ether. There is obtained 90% yield of 2,2,4-trimethyl-1-pentyltosylate.

Similar results are realized with the sodium and potassium perhydro-9b-boraphenalylhydrides.

EXAMPLE 11

To 5 ml. of 1.0M lithium trimethoxyaluminohydride in tetrahydrofuran, under nitrogen, there is added 1.25 ml. of tri-sec-butylborane. After 30 minutes, the flask, which now contains a solution of lithium tri-sec-butylborohydride, is cooled to −78° C. and 1.25 ml. of a 2.0M solution of 4-tert-butylcyclohexanone is introduced. The reaction mixture is stirred for 3 hours before it is hydrolyzed at 25° C. and then oxidized to give 96.5% of cis-4-tert-butylcyclohexanol and 3.5% of the trans-compound.

Alternatively, a 1.0M solution of tri-sec-butylborane in tetrahydrofuran can be heated under reflux with an equivalent quantity of sodium hydride. After 24 hours the solution is cooled. Addition of 2-methylcyclohexanone to this solution at 0°, followed by hydrolysis yields cis-2-methylcyclohexanol in an epimeric purity of 99.3%.

What is claimed is:

1. A borohydride of the formula:

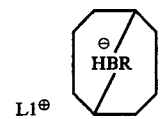

wherein R is an alkyl group containing 3 to 6 carbon atoms and attached to the boron by a secondary or tertiary carbon atom.

2. The borohydride of claim 1 wherein R is thexyl.
3. Lithium 2-thexyl-4,8-dimethyl-2-borabicyclo[3.3.1]-nonylhydride.
4. Lithium tri-(sec-butyl)borohydride.
5. Lithium methyldiisopinocampheylborohydride.
6. Lithium methyldisiamylborohydride.
7. Lithium B-isopropylboracyclohexane hydride.
8. Lithium B-isopropyl-9-borabicyclo[3.3.1]nonanehydride.
9. Lithium perhydro-9b-boraphenalylhydride.

* * * * *